(12) United States Patent
Turner et al.

(10) Patent No.: US 6,225,623 B1
(45) Date of Patent: May 1, 2001

(54) CORONA DISCHARGE ION SOURCE FOR ANALYTICAL INSTRUMENTS

(75) Inventors: Robert Brian Turner, Chesham; Stephen John Taylor, Amersham; Alastair Clark, Watford; Paul Douglas Arnold, Bedford, all of (GB)

(73) Assignee: Graseby Dynamics Limited (GB)

( * ) Notice: Subject to any disclaimer, the term of this patent is extended or adjusted under 35 U.S.C. 154(b) by 0 days.

(21) Appl. No.: 09/126,115

(22) Filed: Jul. 30, 1998

Related U.S. Application Data (63) Continuation of application No. PCT/GB97/00307, filed on Jan. 31, 1997.

(30) Foreign Application Priority Data

Feb. 2, 1996 (GB) .................................................. 9602158

(51) Int. Cl.[7] ............................. B01D 59/44; H01J 49/00
(52) U.S. Cl. ......................................... 250/286; 250/288
(58) Field of Search .................................. 250/281, 288, 250/286, 287

(56) References Cited

U.S. PATENT DOCUMENTS

| | | | |
|---|---|---|---|
| 4,271,357 | * 6/1981 | Bradshaw et al. | 250/287 |
| 5,095,206 | 3/1992 | Bacon, Jr. et al. | |
| 5,234,838 | 8/1993 | Bacon, Jr. | |
| 5,283,199 | * 2/1994 | Bacon et al. | 250/288 |
| 5,491,337 | 2/1996 | Jenkins et al. | |
| 5,684,300 | * 11/1997 | Taylor et al. | 250/288 |

FOREIGN PATENT DOCUMENTS

WO 93/11554   6/1993 (WO).

OTHER PUBLICATIONS

International Search Report mailed May 9, 1997 for International Application No. PCT/GB97/00307.

"Alternative Reagent Ions For Plasma Chromatography," C.J. Proctor, *Analytical Chemistry*, vol. 56, 1984, pp. 1794–1797.

* cited by examiner

Primary Examiner—Bruce C. Anderson
(74) Attorney, Agent, or Firm—Wallenstein & Wagner, Ltd.

(57) ABSTRACT

An ion mobility spectrometer comprises an ion mobility cell (10) into which molecules of a sample to be analysed are introduced. The ion mobility cell (10) is doped with ions produced by a corona discharge ionisation source (40). In one mode of operation, the corona discharge ionisation source (40) operates to produce a continual dopant stream, and in a second mode of operation, the corona discharge ionisation source (40) produces dopant ions selectively. In the non-continuous mode of operation, the ion mobility cell (10) may be doped with chemical dopant ions instead, switching between the two dopant regimes being accomplished very rapidly. The ion mobility spectrometer is particularly suitable for the detection of explosive compounds and narcotics, the ion mobility spectrum of explosives doped with ions from the corona discharge ionisation source differing from the ion mobility spectrum of such explosive compounds doped with chemical dopants.

15 Claims, 12 Drawing Sheets

CORONA DISCHARGE ION SOURCE FOR ANALYTICAL INSTRUMENTS

This Application is a continuation of International Application No. PCT/GB97/00307, filed Jan. 31, 1997, now pending (which is hereby incorporated by reference).

DESCRIPTION

1. Technical Field

The present invention relates to a corona discharge ion source for use in analytical instruments, and in particular for use in ion mobility spectrometers.

2. Background of the Invention

Hitherto, corona discharge sources have been used in ion mobility spectrometers in order to produce the primary ions required for the operation of the instrument. Device is shown in co-pending published PCT application No. WO/9311554.

The principle reason for employing such corona discharge ion sources has been to replace the most frequently used nickel 63 radioactive ionisation source. The corona discharge ion source is significantly cheaper than the nickel 63 source. It is also not subject to the health and safety requirements of a radioactive source and may therefore be more readily transported across borders and so forth.

In substituting a corona ion source for the nickel 63 source, the emphasis has been to replicate as far as possible the ion-molecule chemistry produced by the nickel 63 source, in order to ensure that an ion mobility spectrometer fitted with a corona discharge ionisation source detects the same range of compounds as when fitted with a nickel 63 source.

Figure 4:
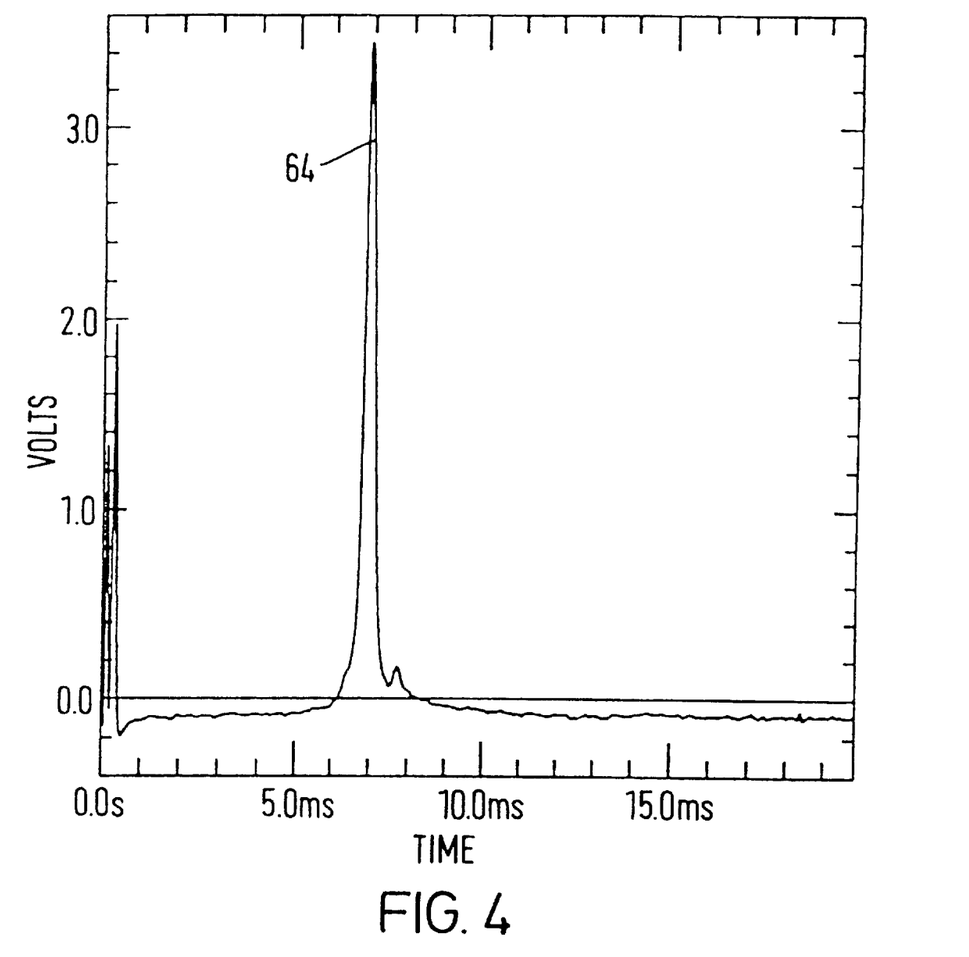
Figure 11:
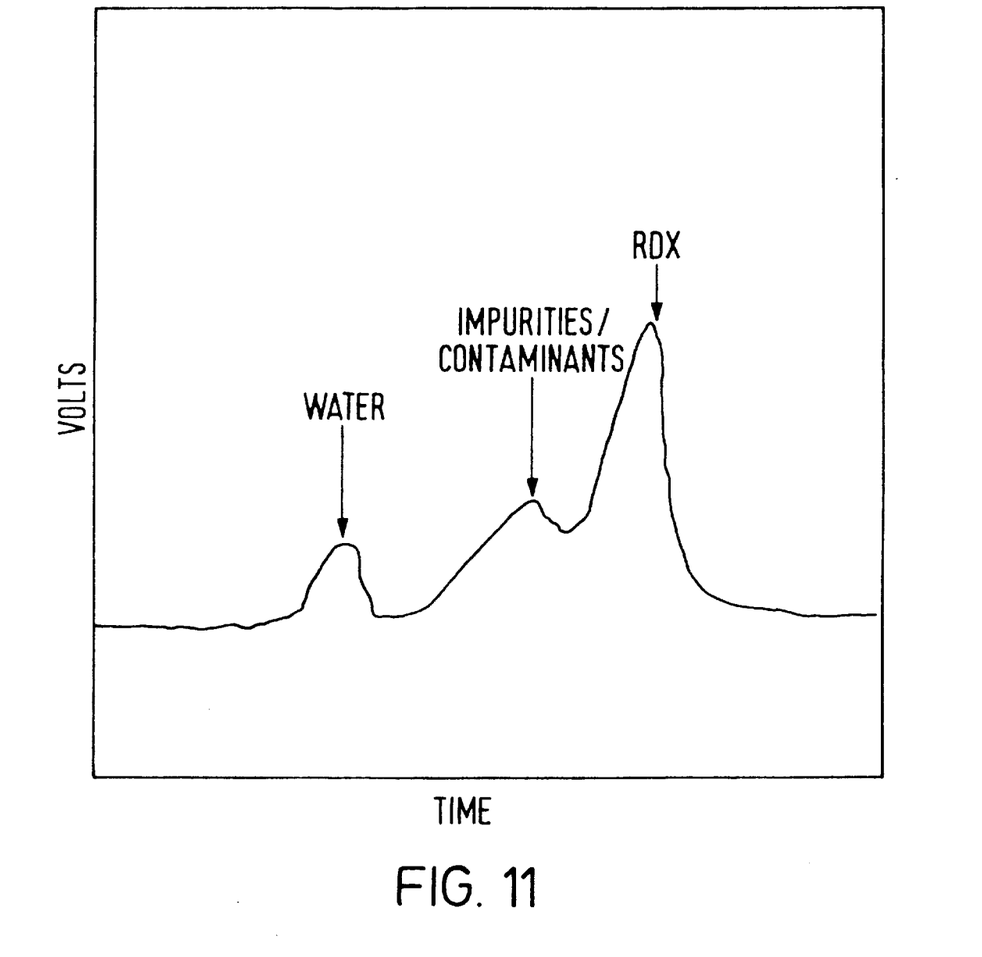
FIG. 11 is a schematic diagram of the output of a prior art ion mobility spectrometer when undoped by chemicals.

FIG. 4 shows a typical output of an ion mobility spectrometer in the absence of an introduced compound or impurity to be detected. This peak corresponds to stable molecular ion species which have resulted from a complex series of ion-molecule reactions and is referred to generally as the Reactant Ion Peak (RIP). When a sample to be detected, such as in this example RDX (a major constituent of Semtex), is introduced into the ion mobility spectrometer, a further peak (or peaks) is detected as well as the reactant ion. The problem with this procedure is that, in practice, the sample entering the ion mobility spectrometer contains a significant number of other compounds. If these have a similar mobility to the RDX ions, the signature peak of the RDX is reduced in amplitude and may in certain cases be suppressed by the contaminants to such an extent that the RDX peak is no longer clearly visible. A schematic plot of the output of an ion mobility spectrometer under these conditions is shown in FIG. 11.

A technique known as chemical doping has been developed to address this problem, and is frequently used in ion mobility spectrometry and chemical ionisation mass spectrometry. Chemical doping may be used irrespective of the ionisation source used to generate the primary ions (i.e. either a corona discharge ion source or a nickel 63 ion source) to change the way in which sample vapour introduced to the device becomes ionised.

The use of such chemical dopants is described in *Analytical Chemistry*, 56(11):1794–1797 by Procter and Todd.

In outline, a chemical dopant, typically in the form of a vapour or gas is introduced into the ionisation region of the instrument such that the dopant chemical becomes the dominant reactant ion species in the ionisation region of the instrument and, if an incoming sample vapour molecule is to be ionised, it must undergo an ion-molecule reaction with the dopant reactant ion.

SUMMARY OF THE INVENTION

According to the present invention, there is provided an analytical instrument including a corona discharge ionisation source arranged to generate corona dopant ions.

When the energy density around the point of a corona discharge is above a certain level, new reaction compounds may be generated. Typically, when the discharge is conducted in air, these compounds will include ozone, oxides of nitrogen and excited neutral states of nitrogen. Since these reaction compounds influence the ion-molecule chemistry in an analytical instrument, previous work has been directed towards minimising the concentration of the compounds, so that their effect on the functioning of the instrument is negligible.

It has been found, however, that the products of the corona discharge ionisation source may be employed as dopant ions, whereby the ion-molecule chemistry of the instrument may be altered under external control.

Preferably, the analytical instrument is an ion mobility spectrometer, the ionisation region of which is doped by the corona dopant ions generated by the corona discharge ionisation source.

By means of, for example, electronic control of the corona discharge, the doping regime of an ion mobility spectrometer may be rapidly and easily altered to provide changing ionisation chemistry conditions, thereby to modify instrument sensitivity and/or selectivity readily.

Preferably, the corona discharge ionisation source is arranged to generate the corona dopant ions substantially continuously. Under such conditions, only a few types of sample vapours, such as explosive compound vapours, are capable of efficient ionisation and hence detection. Thus, the selectivity of the analytical instrument to these compounds is better than that of a system undoped by discharge compounds.

Alternatively, the analytical instrument may have switching means for switching the corona discharge ionisation source such that the dopant ions are generated selectively. Thus, the analytical instrument fitted with a corona discharge ionisation source can, at times, operate under conditions such as to produce the corona dopant ions to dope an ionisation region thereof, and can, at other times, operate under conditions such as not to produce those corona dopant ions, the instrument then operating as an undoped system.

The change between a doped system and an undoped system can be accomplished by electronic switching means, for example, within a very short time, typically within a fraction of a second. Thus a sample vapour administered to the ion mobility spectrometer, for example, could be quickly analysed under two different doping regimes.

Analysis of the sample vapour under the two different regimes provides additional identification information. For instance, the sample vapour may be ionised when the system is undoped, but not when it is doped by the discharge compounds, and this may help to indicate that the sample vapour is not that from an explosive compound. In another case, the mobility of the detected ion may be different under the two doping regimes, and indicate that the ion species formed from the sample vapour is different in the two regimes. This has also provided further discriminatory information, provided that all sample vapours ionised in both regimes did not change their mobility by the same amount.

Preferably, the analytical instrument further comprises chemical dopant means arranged to generate different, chemical dopant ions. Preferably the chemical dopant ions are produced when the corona dopant ions are not being produced by the corona discharge ionisation source. The chemical dopant means may be a gas permeable source fitted within a circulating gas flow of the analytical instrument.

This mode of operation can be of value, for example, if the electron or proton affinity of the corona dopant ions produced by the corona discharge ionisation source are greater than those of the chemical dopant ions available from the permeation source.

If the analytical instrument is an ion mobility spectrometer, then the primary ions necessary for ionisation of a sample to be analysed may either be generated by the corona discharge ionisation source which also generates the corona dopant ions, or alternatively may be generated by a radioactive source, such as nickel 63. In the latter case, the corona discharge ionisation source may not be fitted in the ionisation region of the instrument but instead external to that region, and possibly outside the body of the ion mobility spectrometer, for instance in a gas flow into the instrument. For example, the corona discharge ionisation source may be located in series with an incoming gas flow associated with the cell.

Corona dopant ions generated by the corona discharge would be carried into the cell and act as dopants in the manner described above, without the corona discharge source acting as the means of ionisation of the incoming sample. This method may enable the provision of a high concentration of corona dopant ion into the instrument to more positively dope the cell. Generation of the corona dopant compounds may be controlled electronically to achieve added instrument sensitivity and selectivity.

The corona discharge ionisation source is preferably a pulsed corona ioniser with either a single or a double point source.

BRIEF DESCRIPTION OF THE DRAWINGS

In order that the invention may be more readily understood a specific embodiment will be described by way of example only, with reference to the accompanying drawings in which.

BRIEF DESCRIPTION OF THE PREFERRED EMBODIMENT

Figure 1A:
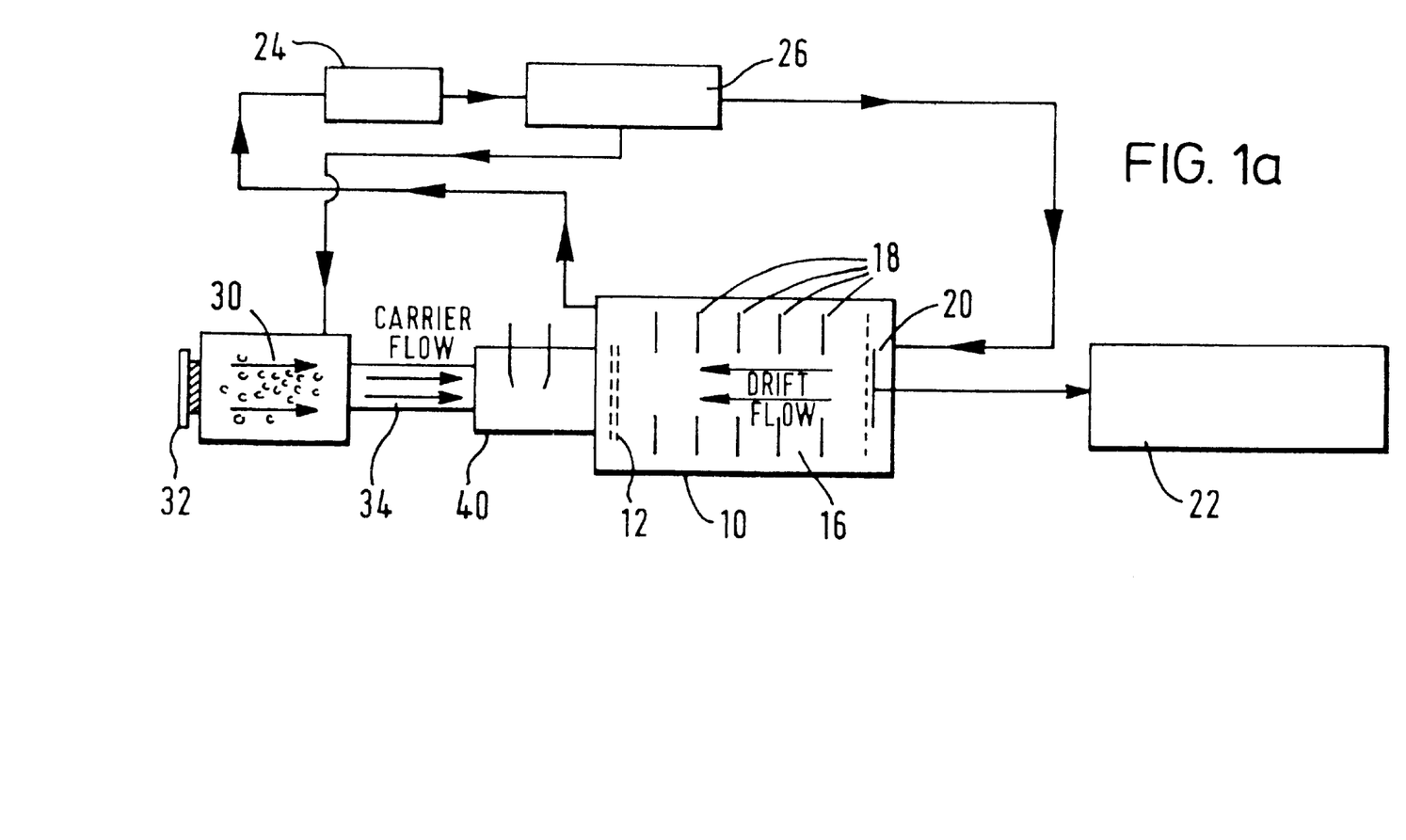
FIG. 1a is a diagrammatic representation of the essential elements of an ion mobility spectrometer used to demonstrate the operation of corona ion source doping, with constant chemical dopant supply.
Figure 1B:
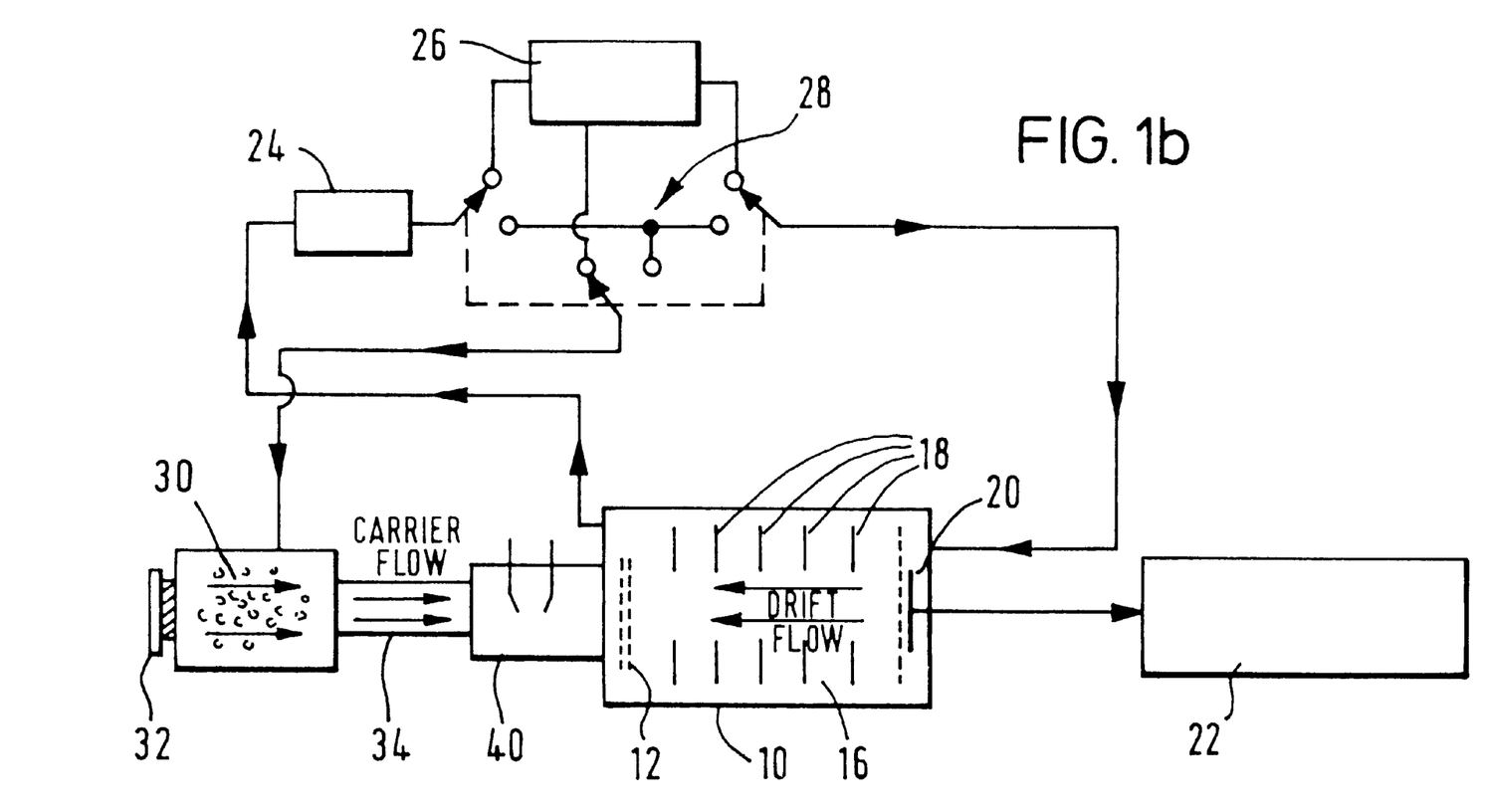
FIG. 1b is the ion mobility spectrometer of FIG. 1a, with a switching arrangement to permit selective doping with the chemical dopant instead of a constant chemical dopant supply.

Referring to FIGS. 1a or 1b, the apparatus used to demonstrate the occurrence and application of corona ion source doping comprises an ion mobility cell 10, having an ion injection gate 12, and a drift region 16, provided with electrodes 18 for establishing an electric drift field along the drift tube 16, and a collector electrode 20.

Sample material is introduced into the ion mobility cell 10 by way of the thermal desorption source 30, and corona ionisation source 40, attached to the ion mobility cell 10 in the region of the ion injection gate 12.

Material introduced into the thermal desorption source 30, by means of a sample wipe 32, is heated sufficiently to cause vapourisation, desorbed vapours being swept, by means of a carrier gas flow through tube 34 into corona ionisation source 40, where ionisation takes place, sample ions, together with any unreacted dopant ions, being swept into ion mobility cell 10, which is operated at a cell temperature of 105° C.

In the conditions pertaining to the plots obtained, the sample is offered to the system in particulate form upon PTFE sample wipes 32. Thermal desorption source 30 provides a stream of dry air at 200° C. directed onto the sample wipe 32 and thus releases analyte vapour into the carrier gas flow through tube 34. The analyte vapour is subsequently swept into the dual point corona discharge ionisation source 40 where, after a series of ion molecule reactions between analyte molecules and reactant ions formed in the source, product ions are formed. These product ions (and usually some unreacted reactant ions) are then gated into the drift region 16 of the cell where they are separated electrically according to their ionic mobilities and detected.

The ion mobility cell 10 is provided with ancillary means such as a pump 24, for establishing the usual carrier and drift gas flows necessary for its proper operation, together with means for establishing the necessary electric drift field by means of potentials applied to electrodes 18, all as well known in the art.

In FIG. 1a, a chemical dopant source 26 is arranged in a circulating gas flow of the analytical instrument, circulation being carried out by means of the pump 24. The chemical dopant source is, for example, a gas permeable source.

FIG. 1b shows a different arrangement to permit the chemical dopant to be added to the ion mobility spectrometer selectively. Switching means 28 is employed within the circulating gas flow. This may include, for example, a valve (not shown). The switch 28 allows the chemical dopant source to be brought into and out of the gas flow circuit, as shown in that Figure.

Figure 2:
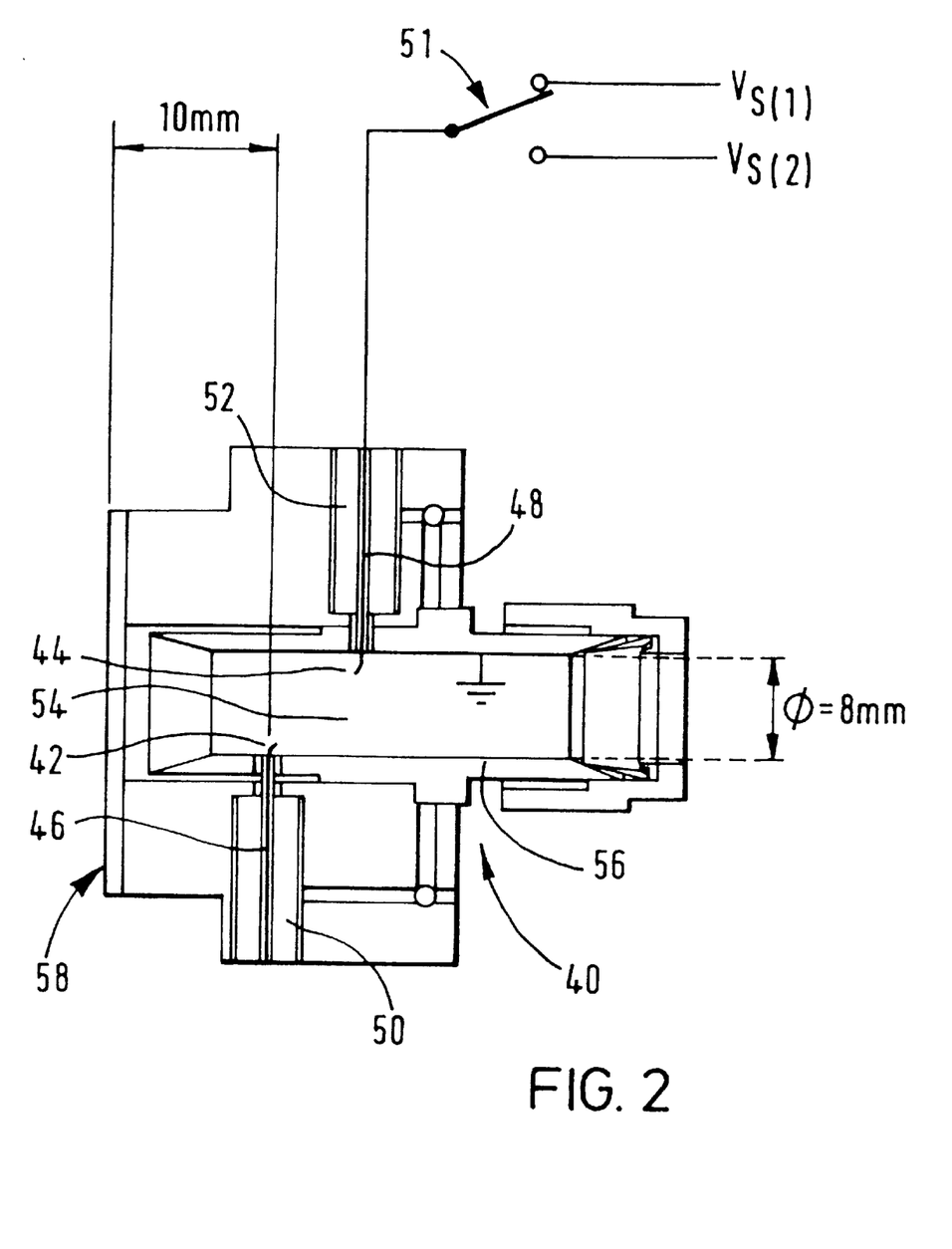
FIG. 2 is a schematic representation of the corona ionisation source employed in the apparatus of FIG. 1.

The essential features of the ioniser are shown in FIG. 2. The corona ionisation source 40 comprises two fine gold wires, 42 and 44, both of 10 μm diameter, spot-welded onto clean tinned copper wires, 46 and 48, located within electrically-insulating Fluorosint holders, 50 and 52. Both points emerge into the source region 54 which has a circular cross-section of diameter 8 mm. During operation, the source block 56 is electrically grounded at all times.

The corona ionisation source 40 described is operated in a pulsed mode thus producing a packet of ions for analysis in the associated ion mobility spectrometer. Ions formed by the source 40 drift towards a standard Bradbury-Nielsen ion gate 58 through which they are injected into the drift space of the ion mobility spectrometer in the normal manner.

The delay between the corona pulse applied to the primary corona point 42, and the gating pulse applied to the ion injection gate 58 is optimised to maximise transmission of ions into the drift space of the spectrometer, which, with the geometry and dimensions of the source 40, is in the range 1 ms to 2 ms.

To achieve satisfactory operation of source 40, both a standing dc voltage and a pulsed voltage are applied to the primary point 42, both of the same polarity as the ions to be generated, whereas the secondary point 44 is held at a dc voltage of opposite polarity to that of the primary point.

The ion-molecule chemistry prevailing in the corona ionisation source 40 of the spectrometer can be altered significantly by switching the secondary point voltage from below to above the threshold voltage required to initiate a self-sustaining dc corona discharge at the secondary point 44.

When the corona discharge at the secondary point 44 is not self-sustaining (i.e. it requires an influence from the primary point to operate) the ion chemistry is to all intents identical to that of an ion mobility spectrometer employing a standard nickel 63 ionisation source, whereas a different ion chemistry (referred to as "leading edge" chemistry) is observed when a self-sustaining corona discharge is established at the secondary point 44.

It is therefore a simple matter to alter the ion chemistry prevailing in the source region 54 by effecting a discrete change in the voltage applied to the secondary point 44. This may be done, for example, using a switch 51 which may be software controlled.

To achieve stable operation in the corona ionisation source 40, the d.c. voltage applied to primary point 42 was set between −300V and −600V and the pulse amplitude between −1.5 kV and −2.5 kV. The experimental conditions were identical for all spectra shown in the accompanying figures of the drawings, with the one exception that the secondary point voltage was set at +800V when operated with normal ion chemistry—with no self-sustained corona discharge on point 44, and at +1100V when operated with "leading edge" chemistry—with a self-sustained discharge on point 44.

Figure 3:
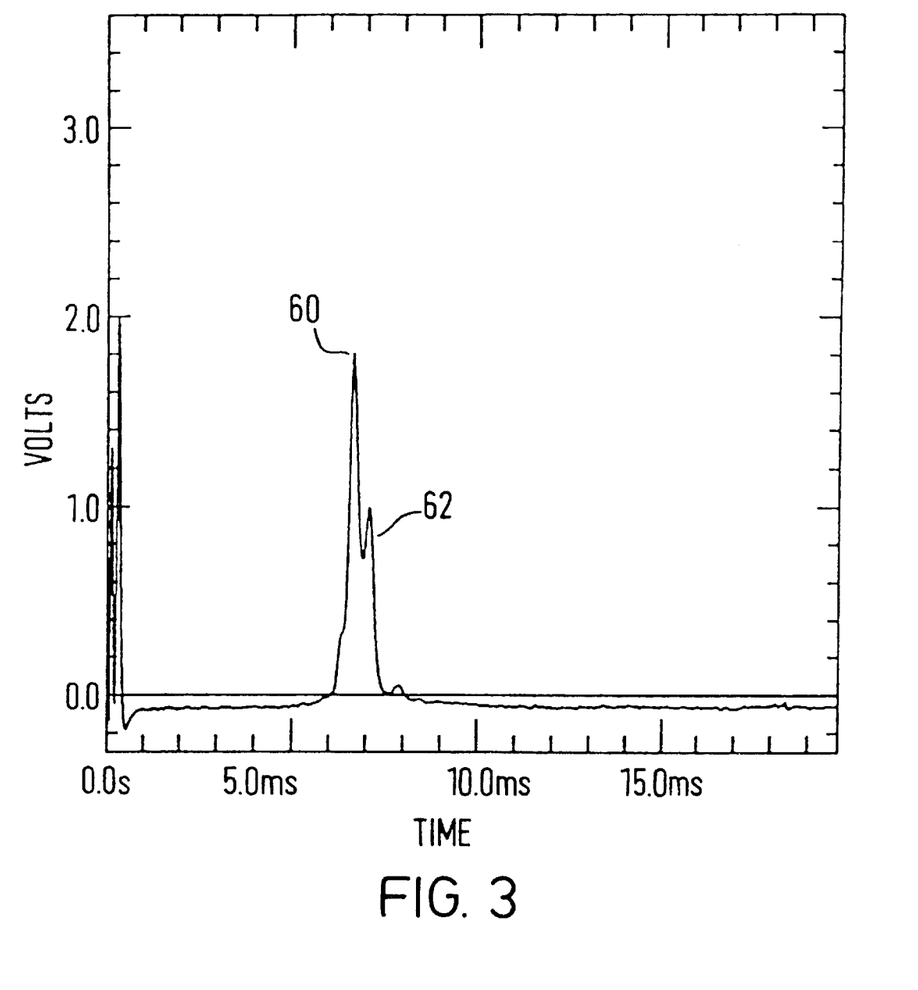
FIGS. 3 and 4 are plots of ion peaks representative of the use, and non-use of corona ionisation source doping in the ion mobility spectrometer of FIG. 1.

The ion-molecule chemistry which prevails in the ionisation region of an ion mobility spectrometer equipped with the pulsed dual-point corona discharge ionisation source 40 described above can be altered significantly by suitable variations of the corona point voltages. Negative ion mobility spectra have been recorded with the corona system operating (a) in a regime where the system response is similar to that of a conventional nickel 63 ionisation source (normal ion chemistry), and (b) where the energy density at either corona point is high enough to introduce an additional ion species into the reaction region. When the latter is the case, a strong ion peak 60 is observed on the leading edge of the normal reactant ion peak 62 as can be seen in FIG. 3. Where such a situation applies, the effect is referred to as "leading edge" chemistry.

FIG. 4 shows the reactant ion peak 64 obtained with normal ion chemistry.

Both spectra were recorded with a clean PTFE sample wipe 32 introduced to the system of FIG. 1, and were averaged over eight ion gate pulses.

All spectra presented in the drawings were signal averaged over eight individual spectra produced during the eight respective ion gate pulses, using a Nicolet 4904 digital oscilloscope fed from the signal processing and analysing circuitry attached to the collector electrode 20 of the ion mobility spectrometer 10, and stored on floppy disk.

RDX, a high explosive, has been selected as a typical demonstration compound, which shows the qualitative differences in the spectra when "normal" and "leading edge" ion chemistry is used.

A quantity of 9 ng of RDX was deposited on a clean sample wipe and offered to the system of FIG. 1. With normal ion chemistry prevailing, three strong product ion peaks 70, 72 and 74 are observed at 9.76, 10.47 and 11.13 ms on the spectrum illustrated in FIG. 5.

Figure 6:
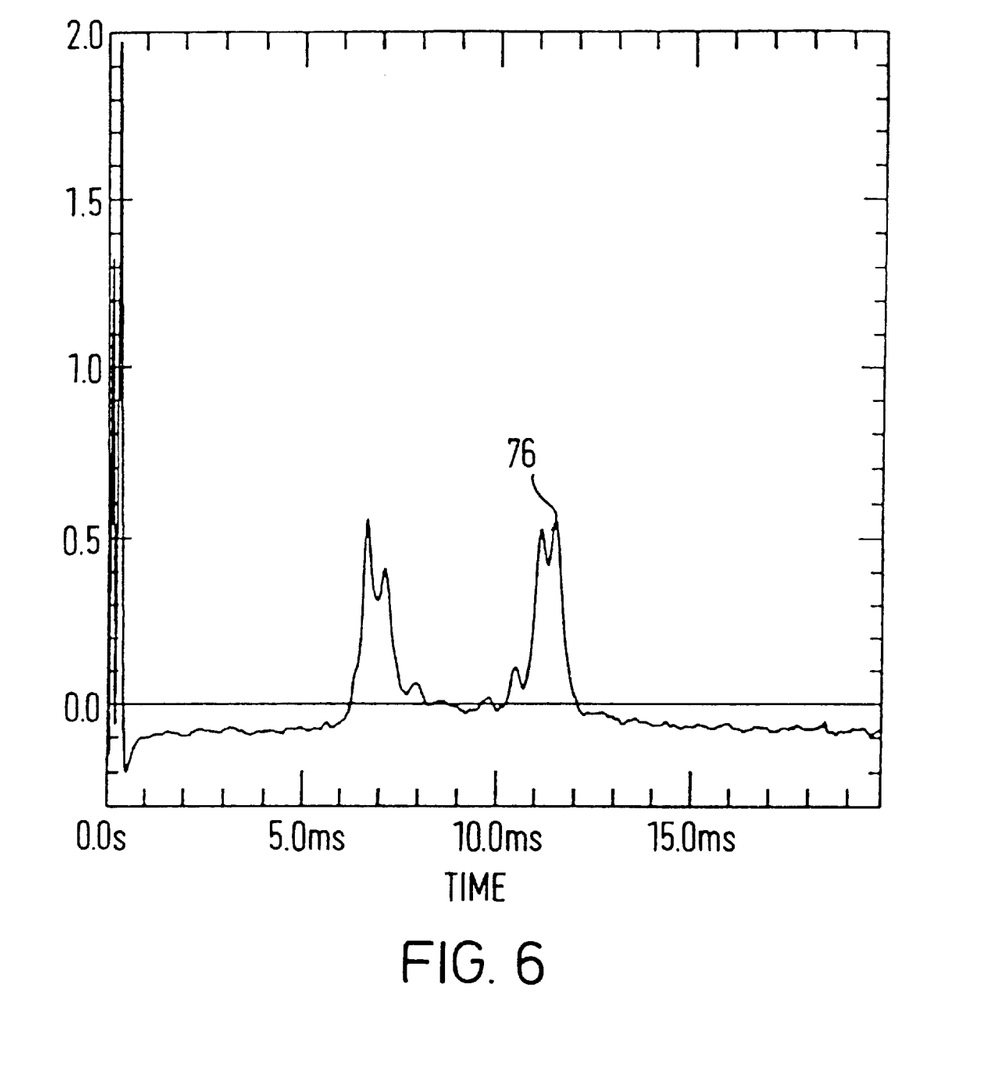

The effect of introducing leading edge chemistry is to suppress the peaks at 9.76 and 10.47 ms and to produce an additional product ion peak 76 at 11.48 ms, as can be seen in FIG. 6. This obvious change in the spectra could be utilised as an additional means of identification for RDX.

Figure 5:
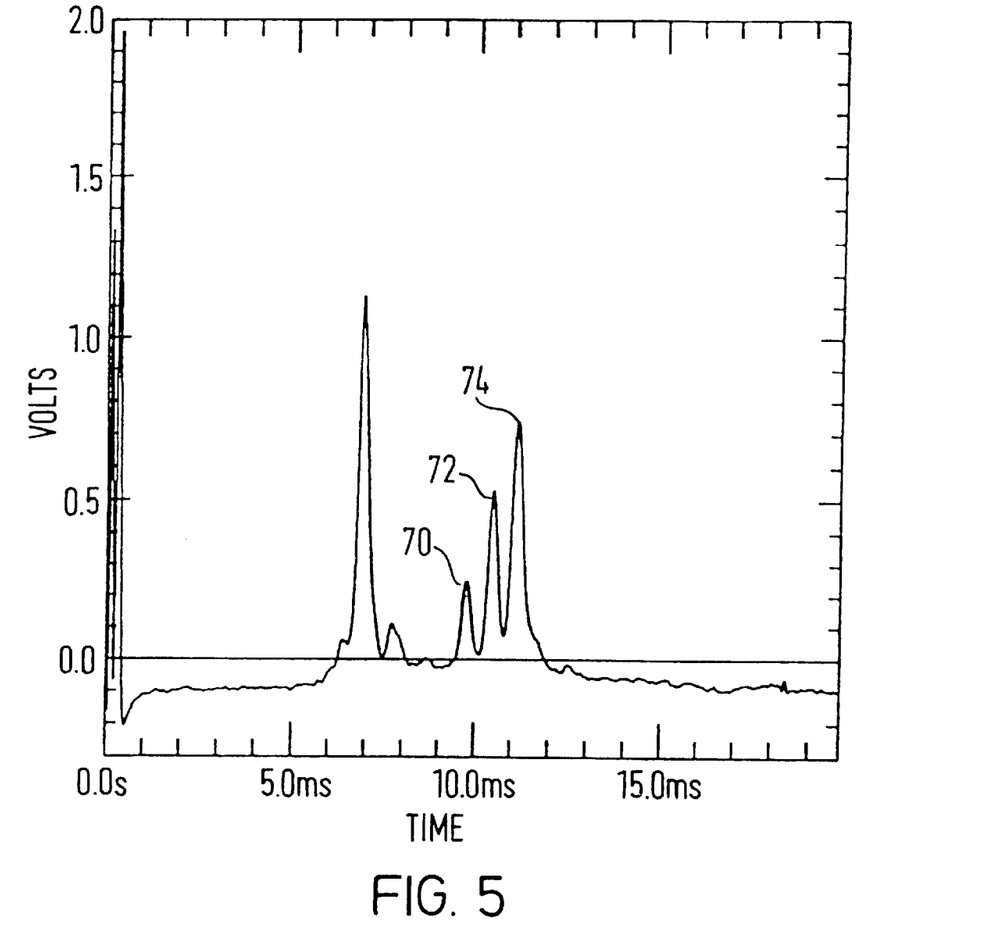
FIGS. 5 to 10 inclusive are plots of ion peaks obtained from the ion mobility spectrometer of FIG. 1, with the introduction of various samples, as described below.

The spectra shown in FIGS. 5 and 6 were recorded for the same sample, as the sample wipe 32 was not removed from the thermal desorption source 30 between chemistry changes.

A clean sample wipe was wiped on a piece of paper which had been contaminated with "WD-40" lubricant and offered to the system of FIG. 1.

Figure 7:
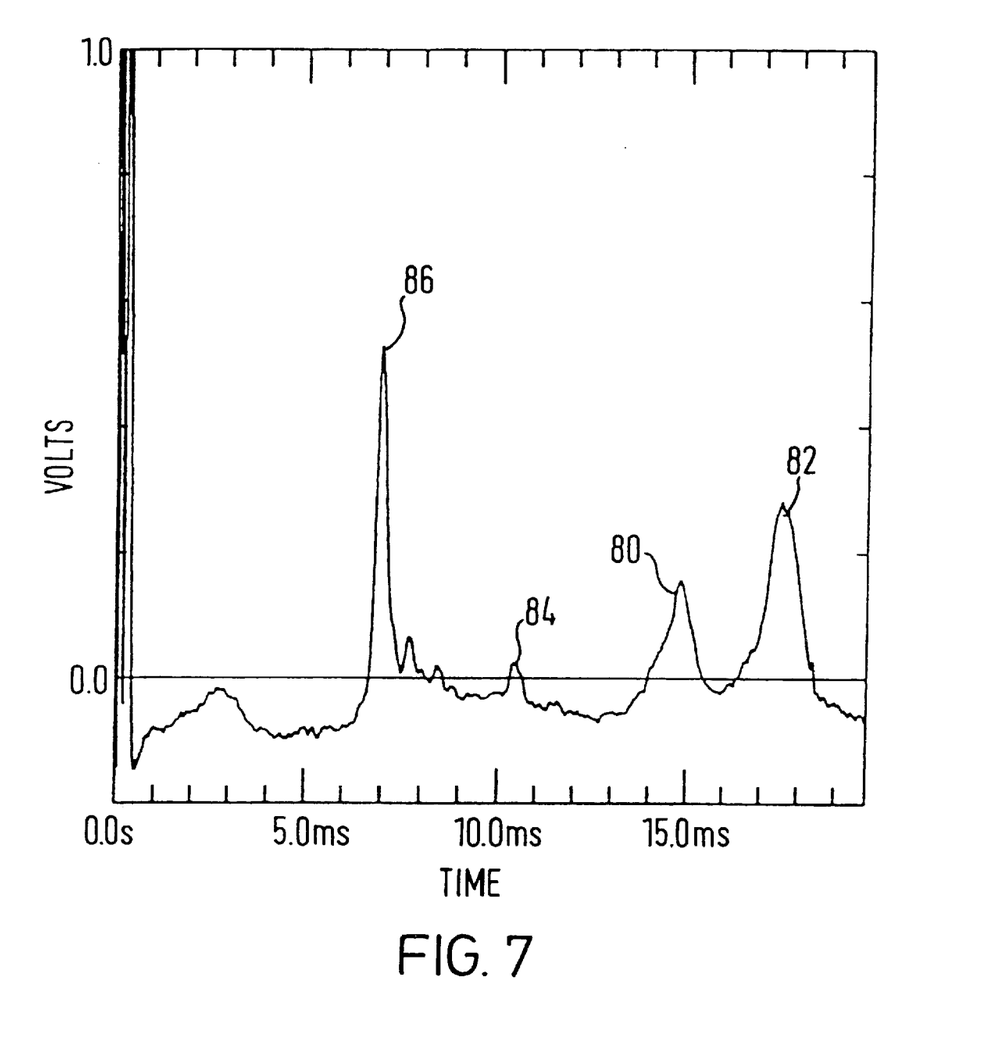

FIG. 7 shows the spectrum obtained with normal ion chemistry.

Figure 8:
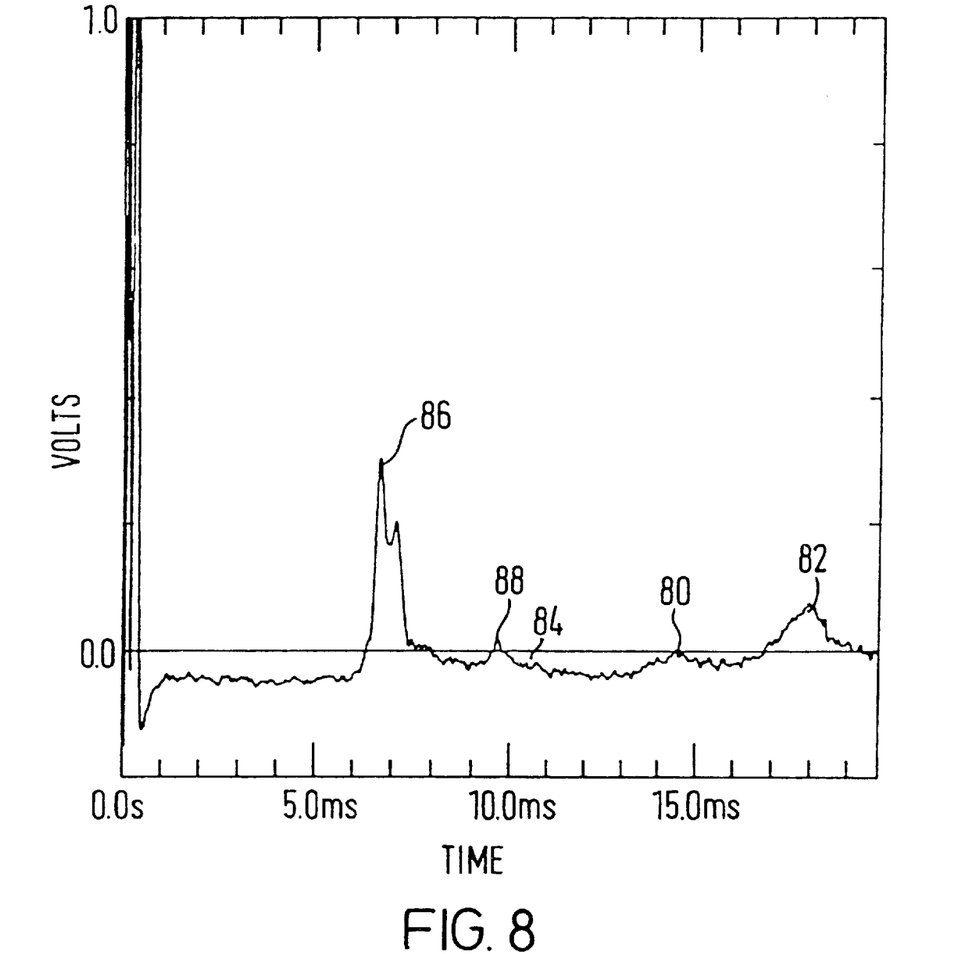

The effect of introducing leading edge chemistry is marked as seen in FIG. 8. The wide peaks 80 and 82 at 14.5 ms and 17.5 ms are greatly reduced in intensity as are the peaks 84 at 10.5 ms, and 86 between 7.0 ms and 9 ms. An additional peak 88, not apparent in the normal chemistry spectrum of FIG. 7, is observed at about 9.6 ms.

Figure 9:
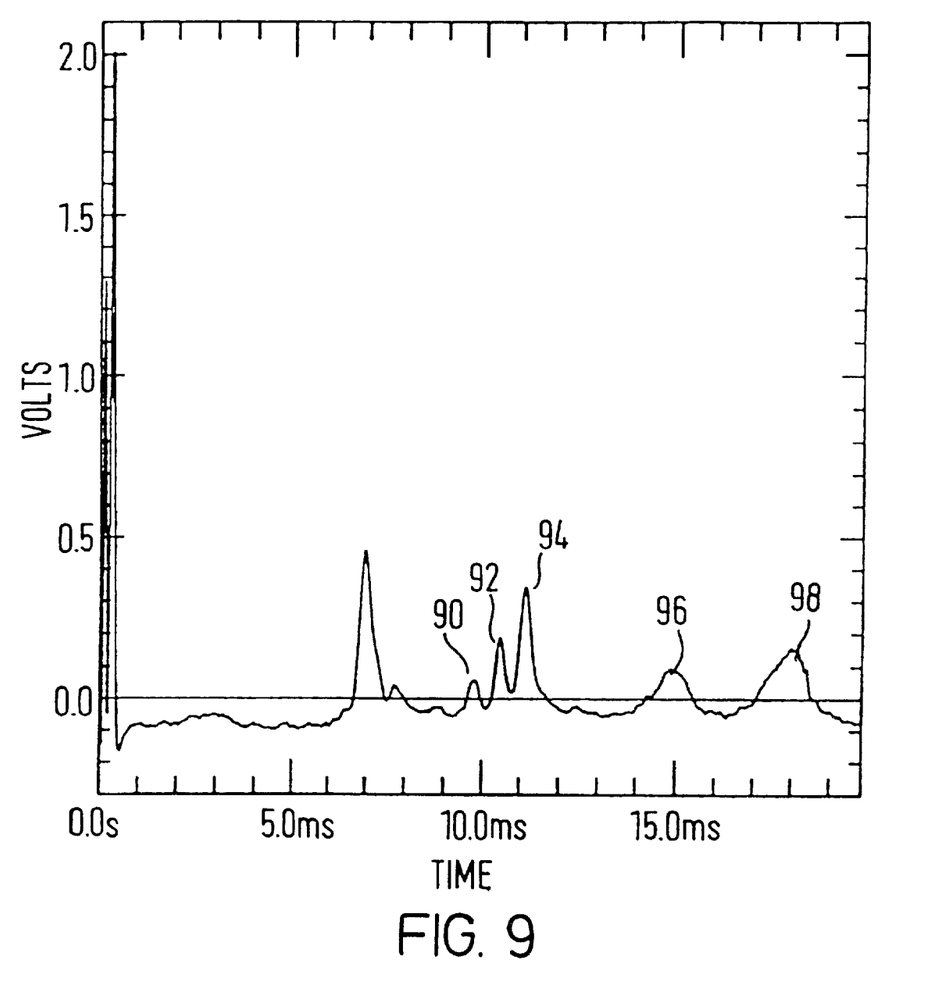
Figure 10:
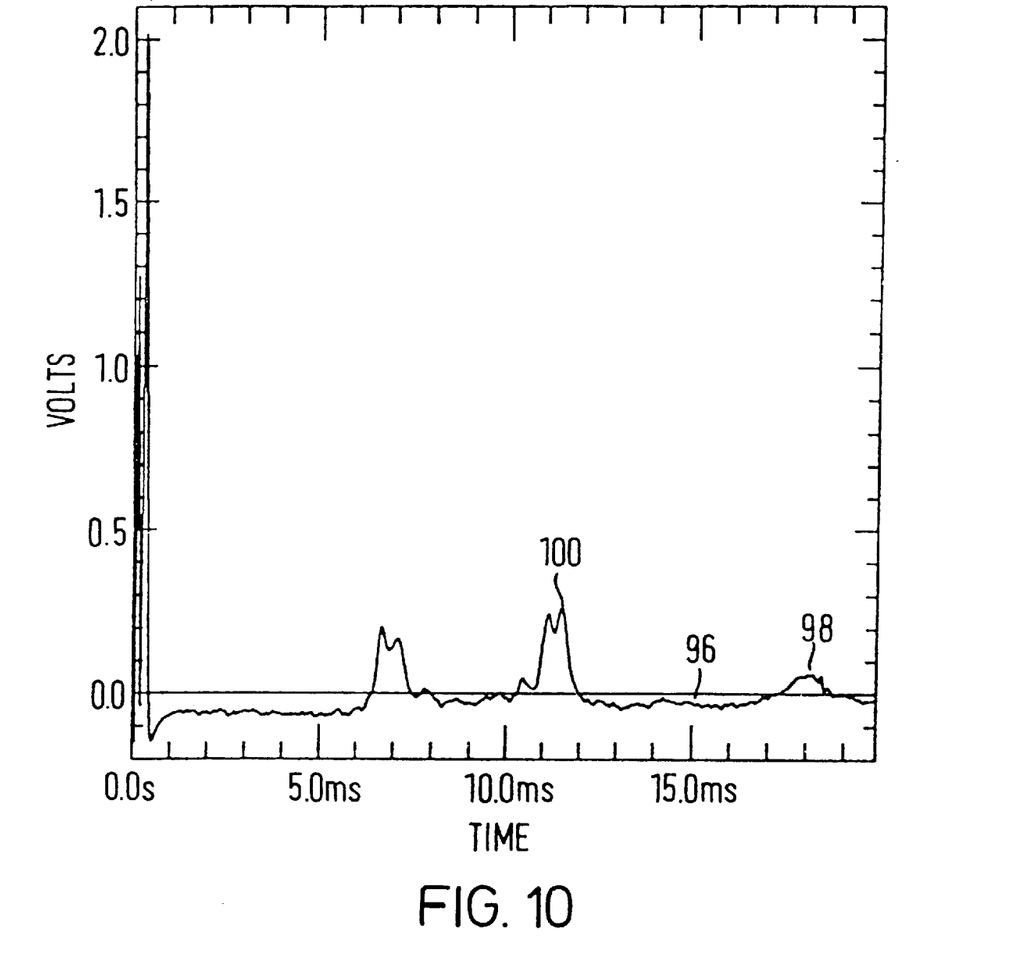

The effect of a "WD-40" background on the response of the system to RDX, with both normal and leading-edge chemistry, is shown in FIGS. 9 and 10.

FIG. 9 shows the spectrum which was obtained from a wipe which had been contaminated with WD-40 and also had 9 ng of RDX deposited upon it. This spectrum was recorded with normal ion chemistry. Clearly, the three product ion peaks 90, 92, 94 associated with RDX vapour are observed as are the broad peaks 96 and 98 corresponding to WD-40 contamination.

However when the instrument of FIG. 1 was operated with leading edge chemistry, FIG. 10 shows that the WD-40 contamination peaks 96 and 98 are suppressed in intensity but the RDX peaks 100, corresponding to the peaks 76 of FIG. 6, persist, thus demonstrating the ability of the system of FIG. 1, when used with ionisation source 40 in the leading-edge mode, to selectively suppress background contamination, without any significant loss in strength of the ion peaks 100 indicative of the presence of RDX.

Although the invention has been described with reference to an application in ion mobility spectrometry, the invention may also be applied in other appropriate instrumental applications where chemical doping has previously been employed.

What is claimed is:

1. An analytical instrument for analyzing a sample comprising:
    an ion mobility spectrometer having a corona discharge ionization source arranged to generate corona dopant ions, the corona discharge ionization source having a primary and a secondary point source;
    a means arranged to change a voltage applied to the secondary point source for controlling the generation of ions; and,
    switching means for selectively generating the corona dopant ions from the secondary point source for analyzing the sample under different doping regimes.

2. The analytical instrument of claim 1, wherein the ion mobility spectrometer has an ionization region that is doped by the corona dopant ions generated by the corona discharge ionization source.

3. The analytical instrument of claim 2, in which the corona discharge ionization source further generates the primary ions for ionization of a sample to be analyzed.

4. The analytical instrument of claim 3, further comprising a radioactive source for generating primary ions for ionization of the sample to be analyzed.

5. The analytical instrument of claim 4, wherein the corona discharge ionization source is positioned outside the ion mobility spectrometer.

6. The analytical instrument of claim 5, wherein the corona discharge ionization source is positioned in a gas flow into the ion mobility spectrometer.

7. The analytical instrument of claim 2, wherein the corona discharge ionization source is a pulsed corona ionizer.

8. The analytical instrument of claim 1, further comprising chemical dopant means arranged to generate different, chemical dopant ions.

9. The analytical instrument of claim 8, wherein the chemical dopant means is a gas permeable source within a circulating gas flow of the analytical instrument.

10. The analytical instrument of claim 1, further analyzing the sample for explosive compounds.

11. An analytical instrument for analyzing a sample comprising:

an ion mobility spectrometer having a corona discharge ionization source arranged to generate corona dopant ions, the corona discharge ionization source having a primary and a secondary point source, and a switching means for selectively generating corona dopant ions from the secondary point source for analyzing the sample under different doping regimes.

12. The analytical instrument of claim 11, wherein the switching means for selectively generating the corona dopant ions from the secondary point source selectively modifies the voltage applied to the secondary point source.

13. The analytical instrument of claim 11 wherein the corona discharge ionization source generates corona dopant ions either substantially continuously or selectively.

14. The analytical instrument of claim 11 wherein the corona discharge ionization source further generates primary ions for ionization of the sample to be analyzed.

15. The analytical instrument of claim 11 further including a radioactive source for generating primary ions for ionization of the sample to be analyzed.

* * * * *

UNITED STATES PATENT AND TRADEMARK OFFICE
CERTIFICATE OF CORRECTION

Page 1 of 1

PATENT NO. : 6,225,623 B1
DATED : May 1, 2001
INVENTOR(S) : Robert Brian Turner et al.

It is certified that error appears in the above-identified patent and that said Letters Patent is hereby corrected as shown below:

Column 7,
Line 1, change "Claim 3" to -- Claim 2 --

Signed and Sealed this

Nineteenth Day of March, 2002

Attest:

JAMES E. ROGAN
Director of the United States Patent and Trademark Office

Attesting Officer